(12) United States Patent
Van Horn

(10) Patent No.: US 12,340,902 B2
(45) Date of Patent: Jun. 24, 2025

(54) METHODS, APPARATUSES, AND COMPUTER PROGRAM PRODUCTS FOR MONITORING ENVIRONMENTAL CONDITIONS

(71) Applicant: Hand Held Products, Inc., Charlotte, NC (US)

(72) Inventor: Erik Van Horn, Seaville, NJ (US)

(73) Assignee: Hand Held Products, Inc., Charlotte, NC (US)

( * ) Notice: Subject to any disclaimer, the term of this patent is extended or adjusted under 35 U.S.C. 154(b) by 230 days.

(21) Appl. No.: 18/074,076

(22) Filed: Dec. 2, 2022

(65) Prior Publication Data

US 2024/0185995 A1 Jun. 6, 2024

(51) Int. Cl.
*G16H 40/63* (2018.01)

(52) U.S. Cl.
CPC ................... *G16H 40/63* (2018.01)

(58) Field of Classification Search
CPC ........ G16H 10/60; G16H 40/63; G16H 50/20; G16H 20/30
See application file for complete search history.

(56) References Cited

U.S. PATENT DOCUMENTS

| | | | |
|---|---|---|---|
| 9,858,794 B2 | 1/2018 | McCleary et al. | |
| 10,212,399 B2 | 2/2019 | Kim et al. | |
| 10,397,751 B2 | 8/2019 | Shapiro et al. | |
| 10,617,302 B2 | 4/2020 | Al-Ali et al. | |
| 10,983,945 B2 | 4/2021 | Molettiere et al. | |
| 11,176,801 B2 | 11/2021 | Kiani | |
| 11,412,938 B2 | 8/2022 | Leboeuf et al. | |
| 2012/0041279 A1* | 2/2012 | Freeman | G16Z 99/00 600/534 |
| 2013/0278414 A1* | 10/2013 | Sprigg | A61B 5/746 340/539.12 |
| 2017/0124276 A1* | 5/2017 | Tee | G16H 40/67 |
| 2021/0076966 A1* | 3/2021 | Grantcharov | G06N 20/00 |
| 2021/0196209 A1* | 7/2021 | Fountaine | G10L 25/66 |

OTHER PUBLICATIONS

Samsung, "Galaxy Note 4: Blood Oxygen Saturation measurement", retrieved from the Internet at URL: <https://www.samsung.com/in/support/mobile-devices/how-accurate-is-the-blood-oxygen-saturation-measurement-in-samsung galaxy-phones/> on May 18, 2023, 3 pages.

* cited by examiner

*Primary Examiner* — Chad A Newton
(74) *Attorney, Agent, or Firm* — ALSTON & BIRD LLP

(57) ABSTRACT

Methods, apparatuses, and computer program products for monitoring environmental conditions are provided. For example, a computer-implemented method may include receiving, over a first time period, a plurality of biometric values from each of a plurality of biometric monitoring devices and detecting an environmental condition based on the received biometric values corresponding to two or more users at a same user location. Each of the plurality of biometric monitoring devices may be worn by a different one of a plurality of users. Each of the plurality of biometric values may be detected from one of the plurality of users and have an associated time of capture and an associated user location at time of capture.

18 Claims, 6 Drawing Sheets

METHODS, APPARATUSES, AND COMPUTER PROGRAM PRODUCTS FOR MONITORING ENVIRONMENTAL CONDITIONS

FIELD OF THE INVENTION

Example embodiments of the present disclosure relate generally to biometric monitoring and, more particularly, to methods, apparatuses, and computer program products for monitoring environmental conditions using biometric monitoring.

BACKGROUND

Environmental hazards are a risk in some workplaces. Employers are always looking for ways to identify and, preferably, prevent workplace hazards. Such environmental hazards may include low oxygen, exposure to carbon monoxide, high temperatures, and the like. Sensors and other environmental monitoring devices may be used to detect environmental hazards. Such environmental monitoring devices must be properly placed throughout the workplace to ensure that hazardous environmental conditions are detected, but it is difficult to ensure complete coverage of an entire workplace to detect all hazardous environmental conditions.

Through applied effort, ingenuity, and innovation, many of these identified problems have been solved by developing solutions that are included in embodiments of the present disclosure, many examples of which are described in detail herein.

BRIEF SUMMARY

Various embodiments described herein relate to methods, apparatuses, and computer program products for monitoring environmental conditions.

In accordance with various embodiments of the present disclosure, an apparatus is provided. In some embodiments, the apparatus comprises at least one processor and at least one non-transitory memory comprising program code. In some embodiments, the at least one non-transitory memory and the program code are configured to, with the at least one processor, cause the apparatus to at least: receive, over a first time period, a plurality of biometric values from each of a plurality of biometric monitoring devices, and detect an environmental condition based on the received biometric values corresponding to at least two or more users at a same user location. Each of the plurality of biometric monitoring devices are worn by a different one of a plurality of users. Each of the plurality of biometric values are detected from one of the plurality of users and have an associated time of capture and an associated user location at time of capture.

In some embodiments, the biometric monitoring devices comprise pulse oximeters and the biometric values comprise oxygen saturation values.

In some embodiments, the at least one non-transitory memory and the program code are configured to, with the at least one processor, cause the apparatus to detect a change in the environmental condition based on one or more changes in the received biometric values corresponding to at least two or more users at a same user location.

In some embodiments, the at least one non-transitory memory and the program code are configured to, with the at least one processor, cause the apparatus to determine a baseline biometric value for each of the plurality of users by receiving, over a second time period and under one or more controlled conditions, a second plurality of biometric values from each of the plurality of biometric monitoring devices.

In some embodiments, the apparatus is adapted to receive the second plurality of biometric values while a user of each of the plurality of biometric monitoring devices performs two or more different tasks.

In some embodiments, the at least one non-transitory memory and the program code are configured to, with the at least one processor, cause the apparatus to detect the environmental condition based on the received biometric values corresponding to two or more users at the same user location by comparing the received biometric values corresponding to two or more users at the same user location to the corresponding baseline biometric value for the two or more users.

In accordance with various embodiments of the present disclosure, a computer-implemented method is provided. In some embodiments, the computer-implemented method comprises receiving, over a first time period, a plurality of biometric values from each of a plurality of biometric monitoring devices and detecting an environmental condition based on the received biometric values corresponding to at least two or more users at a same user location. Each of the plurality of biometric monitoring devices are worn by a different one of a plurality of users. Each of the plurality of biometric values are detected from one of the plurality of users and have an associated time of capture and an associated user location at time of capture.

In accordance with various embodiments of the present disclosure, a computer program product is provided. In some embodiments, the computer program product comprises at least one non-transitory computer-readable storage medium having computer-readable program code portions stored therein. In some embodiments, the computer-readable program code portions comprise an executable portion configured to receive, over a first time period, a plurality of biometric values from each of a plurality of biometric monitoring devices and detect an environmental condition based on the received biometric values corresponding to at least two or more users at a same user location. Each of the plurality of biometric monitoring devices are worn by a different one of a plurality of users. Each of the plurality of biometric values are detected from one of the plurality of users and have an associated time of capture and an associated user location at time of capture.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which.

DETAILED DESCRIPTION OF THE INVENTION

Figure 1:
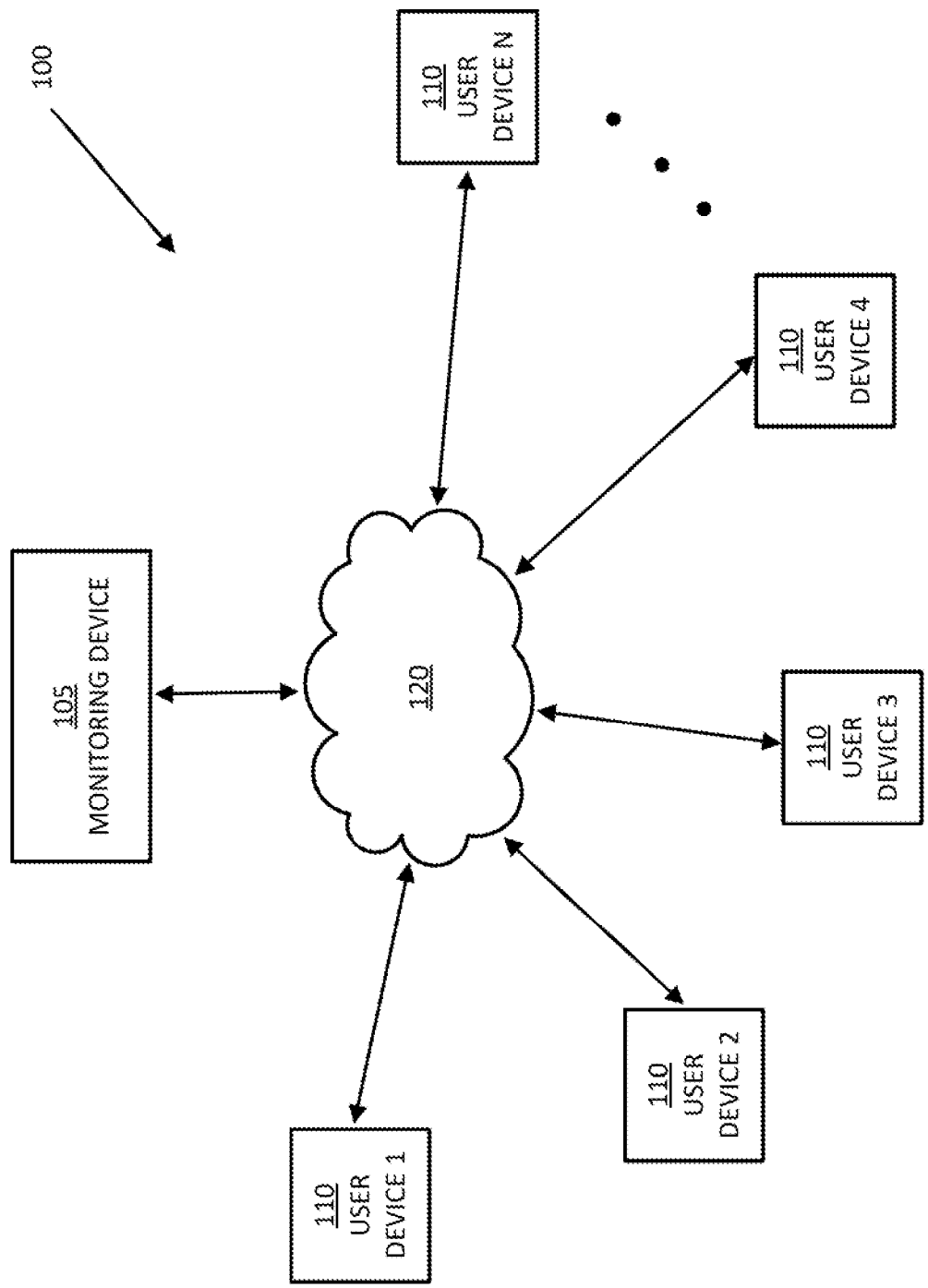
FIG. 1 illustrates an example block diagram of an example system for monitoring environmental conditions in accordance with example embodiments of the present disclosure.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

As used herein, terms such as "front," "rear," "top," etc. are used for explanatory purposes in the examples provided below to describe the relative position of certain components or portions of components. Furthermore, as would be evident to one of ordinary skill in the art in light of the present disclosure, the terms "substantially" and "approximately" indicate that the referenced element or associated description is accurate to within applicable engineering tolerances.

As used herein, the term "comprising" means including but not limited to and should be interpreted in the manner it is typically used in the patent context. Use of broader terms such as comprises, includes, and having should be understood to provide support for narrower terms such as consisting of, consisting essentially of, and comprised substantially of.

The phrases "in one embodiment," "according to one embodiment," "in some embodiments," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such a component or feature may be optionally included in some embodiments, or it may be excluded.

The term "electronically coupled," "electronically coupling," "electronically couple," "in communication with," "in electronic communication with," or "connected" in the present disclosure refers to two or more elements or components being connected through wired means and/or wireless means, such that signals, electrical voltage/current, data and/or information may be transmitted to and/or received from these elements or components.

Various embodiments of the present disclosure provide environmental monitoring by monitoring one or more biometric values (including but not limited to oxygen saturation (SpO2), carbon monoxide (CO) levels, carbon dioxide (CO2) levels, heart rate, respiratory rate, body temperature, etc.) from a plurality of users. One or more potentially hazardous environmental conditions (including but not limited to low atmospheric oxygen levels, elevated atmospheric CO or CO2 levels, elevated temperature, etc.) can be determined based on the users' biometric values and/or changes in the users' biometric values. Example embodiments of the disclosure will be described herein in relation to monitoring SpO2 levels and determining potentially hazardous low atmospheric oxygen levels based on users' SpO2 levels.

In example embodiments, each of a plurality of users will be assigned a wearable device capable of monitoring one or more biometric values and location of its user. The monitoring may be performed continuously or at predetermined intervals (e.g., every minute or every five minutes) while the device is worn and monitoring is desired. In example embodiments, the users may be workers in a workplace. Any suitable wearable device capable of monitoring one or more biometric values and location of its user may be used. In some embodiments, the wearable device will be a smart watch. In example embodiments, the wearable devices will transmit the users' monitored biometric values and associated locations to a central monitoring device, such as a central server or the like. The users' monitored biometric values and associated locations may be transmitted continuously, as they are detected, or stored on the wearable device and transmitted periodically (e.g., every minute or every five minutes). The central monitoring device will analyze the monitored biometric values and associated locations to identify potentially hazardous environmental conditions.

Referring now to the figures, FIG. 1 is an example block diagram of an example system for environmental monitoring in accordance with example embodiments of the present disclosure. FIG. 1 illustrates an example environmental monitoring system 100 that monitors one or more biometric signals and corresponding locations from a plurality of users and analyzes the biometric signal and user location data to identify potentially hazardous environmental conditions. In the illustrated embodiment, the environmental monitoring system 100 comprises a plurality of user wearable devices 110 in communication with a central monitoring device 105 over a network 120. In example embodiments, any suitable number of wearable devices 110 (and associated users) may be monitored. In the illustrated embodiment, the wearable devices 110 are labeled 1 to N to indicate the potentially varying number of devices.

Figure 2:
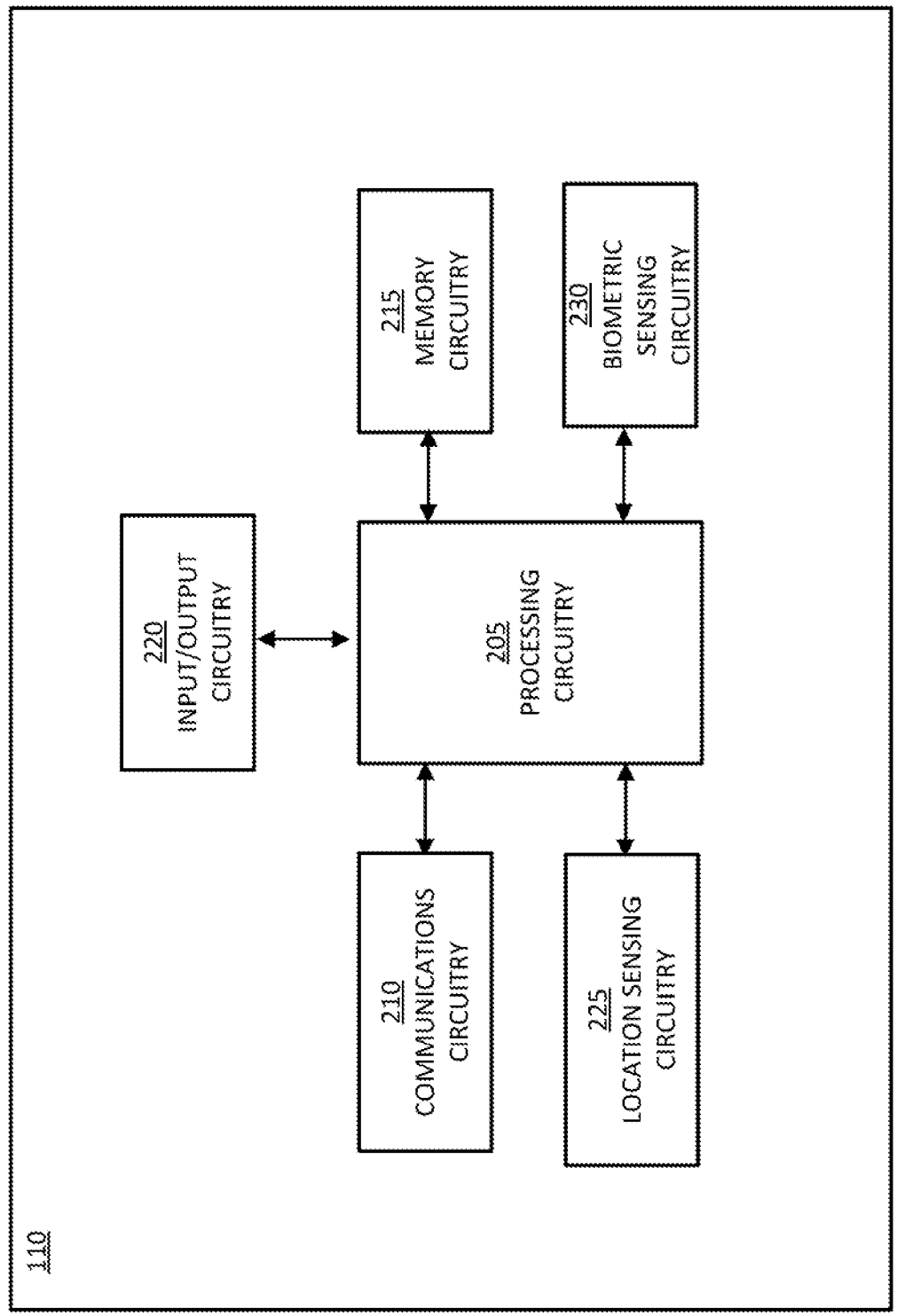
FIG. 2 illustrates an example block diagram of an example user wearable device for monitoring environmental conditions in accordance with example embodiments of the present disclosure.

FIG. 2 is an example block diagram of an example user wearable device for environmental monitoring in accordance with example embodiments of the present disclosure. FIG. 2 illustrates an example user wearable device 110 (such as a smart watch or the like) that can be worn by a user, detect one or more of the user's biometric signals and the user's corresponding location when the biometric signal is detected, and transmit the biometric signals and associated locations to the central monitoring device 105. In the illustrated embodiment, the user wearable device 110 comprises processing circuitry 205, communications circuitry 210, memory circuitry 215, input/output circuitry 220, location sensing circuitry 225, and biometric sensing circuitry 230.

In an example embodiment, the processing circuitry 205 controls the operation of the wearable device 110 and its various components, typically according to configuration data and instructional programming stored in the memory circuitry 215. The processing circuitry 205 can detect the user's location via the location sensing circuitry 225 and detect the user's biometric signal (SpO2 in an example embodiment) via the biometric sensing circuitry 230. In an example embodiment, the location sensing circuitry 225 comprises global positioning system (GPS) circuitry for location detection, but any suitable location tracking circuitry may be used, including but not limited to radio frequency identification (RFID), radio tracking, near-field communication (NFC), and geofencing circuitry. In an example embodiment, the biometric sensing circuitry 230 comprises one or more light emitting diodes (LED) and one or more photodiodes to perform reflectance pulse oximetry for detecting a user's SpO2. The communications circuitry 210 enables the wearable device 110 to communicate with the central monitoring device 105 to transmit the user's location and biometric signal, such as via the network 120. In an example embodiment, the wearable device 110 also has typical smart watch functionality, such as a clock and a timer. In an example embodiment, the input/output circuitry 220 enables the user to interface with the typical smart watch type features of the wearable device 110, such as setting and turning off a timer.

Figure 3:
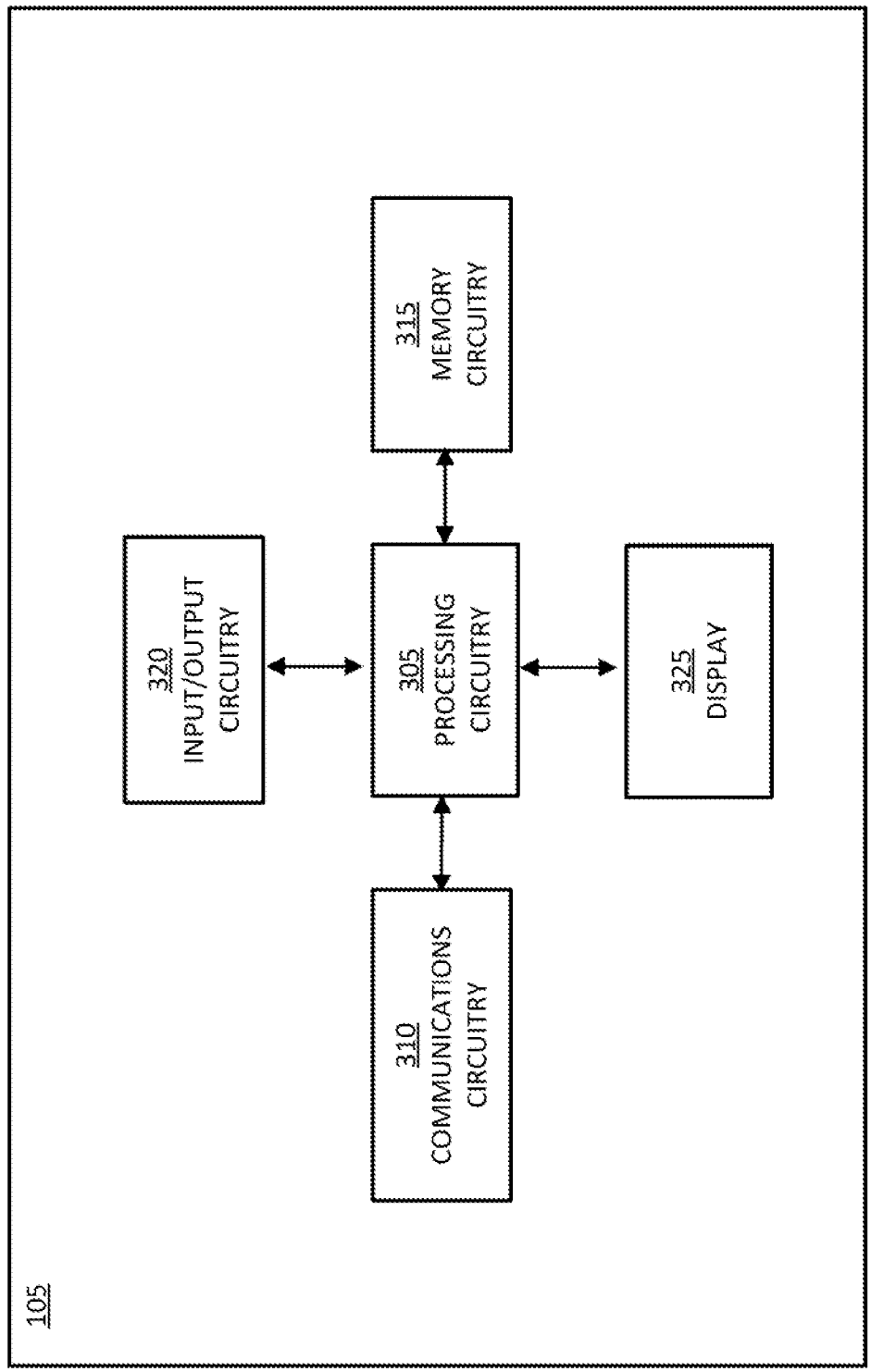
FIG. 3 illustrates an example block diagram of an example central monitoring device for monitoring environmental conditions in accordance with example embodiments of the present disclosure.

FIG. 3 is an example block diagram of an example central monitoring device for environmental monitoring in accordance with example embodiments of the present disclosure. FIG. 3 illustrates an example central monitoring device 105 that can communicate with the wearable devices 110 to receive biometric signals and corresponding locations from a plurality of users and analyze the received data to detect potentially hazardous environmental conditions based on the biometric signals from multiple users. In the illustrated embodiment, the central monitoring device 105 comprises processing circuitry 305, communications circuitry 310, memory circuitry 315, input/output circuitry 320, and a display 325.

In an example embodiment, the processing circuitry 305 controls the operation of the central monitoring device 105 and its various components, typically according to configuration data and instructional programming stored in the memory circuitry 315. The communications circuitry 310 enables the central monitoring device 105 to communicate with the wearable device 110 to receive the user's location and biometric signal, such as via the network 120. The processing circuitry 305 can analyze the received biometric signals and corresponding locations to detect potentially hazardous environmental conditions based on the biometric signals from multiple users, as described further below, and display information and/or alerts related to potentially hazardous environmental conditions for one or more users to view, such as via display 325. In various examples of the present disclosure, the display 325 may include a liquid crystal display (LCD), a light-emitting diode (LED) display, a plasma (PDP) display, a quantum dot (QLED) display, and/or the like. Additionally or alternatively, in various examples of the present disclosure, such information and/or alerts related to potentially hazardous environmental conditions may be transmitted to one or more user communications devices (e.g., mobile phone or the like) for a user to view. The input/output circuitry 320 enables a user to interact with the central monitoring device 105.

The central monitoring device 105 and/or the wearable devices 110 may be configured to execute the operations described herein. Although the components are described with respect to functional limitations, it should be understood that the particular implementations necessarily include the use of particular hardware. It should also be understood that certain of the components described herein may include similar or common hardware. For example, two sets of circuitries may both leverage use of the same processor, network interface, storage medium, or the like to perform their associated functions, such that duplicate hardware is not required for each set of circuitries.

The use of the term "circuitry" as used herein with respect to components of the apparatus should therefore be understood to include particular hardware configured to perform the functions associated with the particular circuitry as described herein. The term "circuitry" should be understood broadly to include hardware and, in some embodiments, software for configuring the hardware. For example, in some embodiments, "circuitry" may include processing circuitry, storage media, network interfaces, input/output devices, and the like. In some embodiments, other elements of the environmental monitoring system 100 may provide or supplement the functionality of particular circuitry. For example, the processing circuitry 205, 305 may provide processing functionality, the communications circuitry 210, 310 may provide network interface functionality, the memory circuitry 215, 315 may provide storage functionality, and the like.

In some embodiments, the processing circuitry 205, 305 (and/or co-processor or any other processing circuitry assisting or otherwise associated with the processor) may be in communication with the memory circuitry 215, 315 via a bus for passing information among components of the apparatus. The processing circuitry 205, 305 may be embodied in a number of different ways and may, for example, include one or more processing devices configured to perform independently. Additionally, or alternatively, the processing circuitry 205, 305 may include one or more processors configured in tandem via a bus to enable independent execution of instructions, pipelining, and/or multithreading. The use of the term "processing circuitry" may be understood to include a single core processor, a multi-core processor, multiple processors internal to the apparatus, and/or remote or "cloud" processors.

For example, the processing circuitry 205, 305 may be embodied as one or more complex programmable logic devices (CPLDs), microprocessors, multi-core processors, co-processing entities, application-specific instruction-set processors (ASIPs), and/or controllers. Further, the processing circuitry 205, 305 may be embodied as one or more other processing devices or circuitry. The term circuitry may refer to an entirely hardware embodiment or a combination of hardware and computer program products. Thus, the processing circuitry 205, 305 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing circuitry 205, 305 may be configured for a particular use or configured to execute instructions stored in volatile or non-volatile media or otherwise accessible to the processing circuitry 205, 305. As such, whether configured by hardware or computer program products, or by a combination thereof, the processing circuitry 205, 305 may be capable of performing steps or operations according to embodiments of the present disclosure when configured accordingly.

In an example embodiment, the processing circuitry 205, 305 may be configured to execute instructions stored in the memory circuitry 215, 315 or otherwise accessible to the processor. Alternatively, or additionally, the processing circuitry 205, 305 may be configured to execute hard-coded functionality. As such, whether configured by hardware or software methods, or by a combination thereof, the processor may represent an entity (e.g., physically embodied in circuitry) capable of performing operations according to an embodiment of the present disclosure while configured accordingly. Alternatively, as another example, when the processing circuitry 205, 305 is embodied as an executor of software instructions, the instructions may specifically configure the processor to perform the algorithms and/or operations described herein when the instructions are executed.

In some embodiments, the memory circuitry 215, 315 may further include or be in communication with volatile media (also referred to as volatile storage, memory, memory storage, memory circuitry and/or similar terms used herein interchangeably). In some embodiments, the volatile storage or memory may also include, such as but not limited to, RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the memory circuitry 215, 315 may be used to store at least portions of the databases, database instances, database management system entities, data, applications, programs, program modules, scripts, source code, object code, byte code, compiled code, interpreted code, machine code, executable instructions, and/or the like being executed by, for example, the processing circuitry 205, 305 as shown in FIGS. 2 and 3. Thus, the databases, database instances, database management system entities, data, applications, programs, program modules, scripts, source code, object code, byte code, compiled code, interpreted code, machine code, executable instructions, and/or the like may be used to control certain aspects of the operation of the central monitoring device 105 and/or the wearable devices 110 with the assistance of the processing circuitry 205, 305 and operating system.

In some embodiments, the memory circuitry 215, 315 may further include or be in communication with non-volatile media (also referred to as non-volatile storage, memory, memory storage, memory circuitry and/or similar terms used herein interchangeably). In some embodiments, the memory circuitry 215, 315 may include, such as, but not limited to, hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the memory circuitry 215, 315 may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to may refer to a structured or unstructured collection of information/data that is stored in a computer-readable storage medium.

In various embodiments of the present disclosure, the memory circuitry 215, 315 may also be embodied as a data storage device or devices, as a separate database server or servers, or as a combination of data storage devices and separate database servers. Further, in some embodiments, memory circuitry 215, 315 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the recovery system may be stored. Further, the information/data required for the operation of the recovery system may also be partially stored in the cloud data storage system and partially stored in a locally maintained data storage system. More specifically, memory circuitry 215, 315 may encompass one or more data stores configured to store information/data usable in certain embodiments.

In the example as shown in FIGS. 2 and 3, one or more instances of circuitry may be part of the memory circuitry 215, 315. In this example, the term "circuitry" refers to one or more data storage units in the memory circuitry 215, 315 that may store executable computer program instructions. When the executable computer program instructions stored in such circuitry are executed by a processing circuitry (such as, but not limited to, the processing circuitry 205, 305 shown in FIGS. 2 and 3), the executable computer program instructions may cause the processing circuitry to perform one or more functions.

The communications circuitry 210, 310 may be any means such as a device or circuitry embodied in either hardware or a combination of hardware and software that is configured to receive and/or transmit data from/to a network and/or any other device, circuitry, or module in communication with the central monitoring device 105 and/or the wearable devices 110. In this regard, the communications circuitry 210, 310 may include, for example, a network interface for enabling communications with a wired or wireless communication network and/or in accordance with a variety of networking protocols described herein. For example, the communications circuitry 210, 310 may include one or more network interface cards, antennae, buses, switches, routers, modems, and supporting hardware and/or software, or any other device suitable for enabling communications via a network. Additionally, or alternatively, the communication interface may include the circuitry for interacting with the antenna(s) to cause transmission of signals via the antenna(s) or to handle receipt of signals received via the antenna(s).

It is also noted that all or some of the information discussed herein can be based on data that is received, generated and/or maintained by one or more components of the central monitoring device 105 and/or the wearable devices 110. In some embodiments, one or more external systems (such as a remote cloud computing and/or data storage system) may also be leveraged to provide at least some of the functionality discussed herein.

FIG. 1 depicts a central monitoring device 105 in communication with multiple wearable devices 110. In some embodiments, the central monitoring device 105 and/or the wearable devices 110 are configured to communicate with each other directly or indirectly through direct communication with another device (e.g., a controller). In other embodiments, for example as depicted, the central monitoring device 105 and/or the wearable devices 110 are configured to communicate with each other over a communications network 120.

The communications network 120 may embody any of a myriad of network(s) configured to enable communication between two or more computing device(s). In some embodiments, the communications network 120 embodies a private network. For example, the central monitoring device 105 may be embodied by various computing device(s) on an internal network, such as one or more server(s) of a warehouse in communication with the various wearable devices 110 worn by various workers in the warehouse.

In other embodiments, the communications network 120 embodies a public network, for example the Internet. In some such embodiments, the central monitoring device 105 may embody a remote or "cloud" system that accesses the wearable devices 110 over the communications network 120 from a location separate from the physical location of the wearable devices 110. For example, the central monitoring device 105 may be embodied by computing device(s) of a central headquarters, server farm, distributed platform, and/ or the like. In some such embodiments, the central monitoring device 105 may be accessed directly (e.g., via a display and/or peripherals operatively engaged with the central monitoring device 105), and/or may be accessed indirectly through use of a client device. For example, in some embodiments, a user may login (e.g., utilizing a username and password) or otherwise access the central monitoring device 105 to access the described functionality with respect to one or more particular warehouses, manufacturing facilities, and/or the like.

In some embodiments, the input/output circuitry 220, 320 may be in communication with, respectively, the processing circuitry 205, 305 to provide output to the user and, in some embodiments, to receive an indication of a user input. The input/output circuitry 220, 320 may include a keyboard, a mouse, a joystick, a touch screen, touch areas, soft keys, a microphone, a speaker, or other input/output mechanisms. The processor and/or user interface circuitry comprising the processor may be configured to control one or more functions of one or more user interface elements through computer program instructions (e.g., software and/or firmware) stored on a memory accessible to the processor (e.g., the memory circuitry 215, 315, and/or the like).

Figure 4:
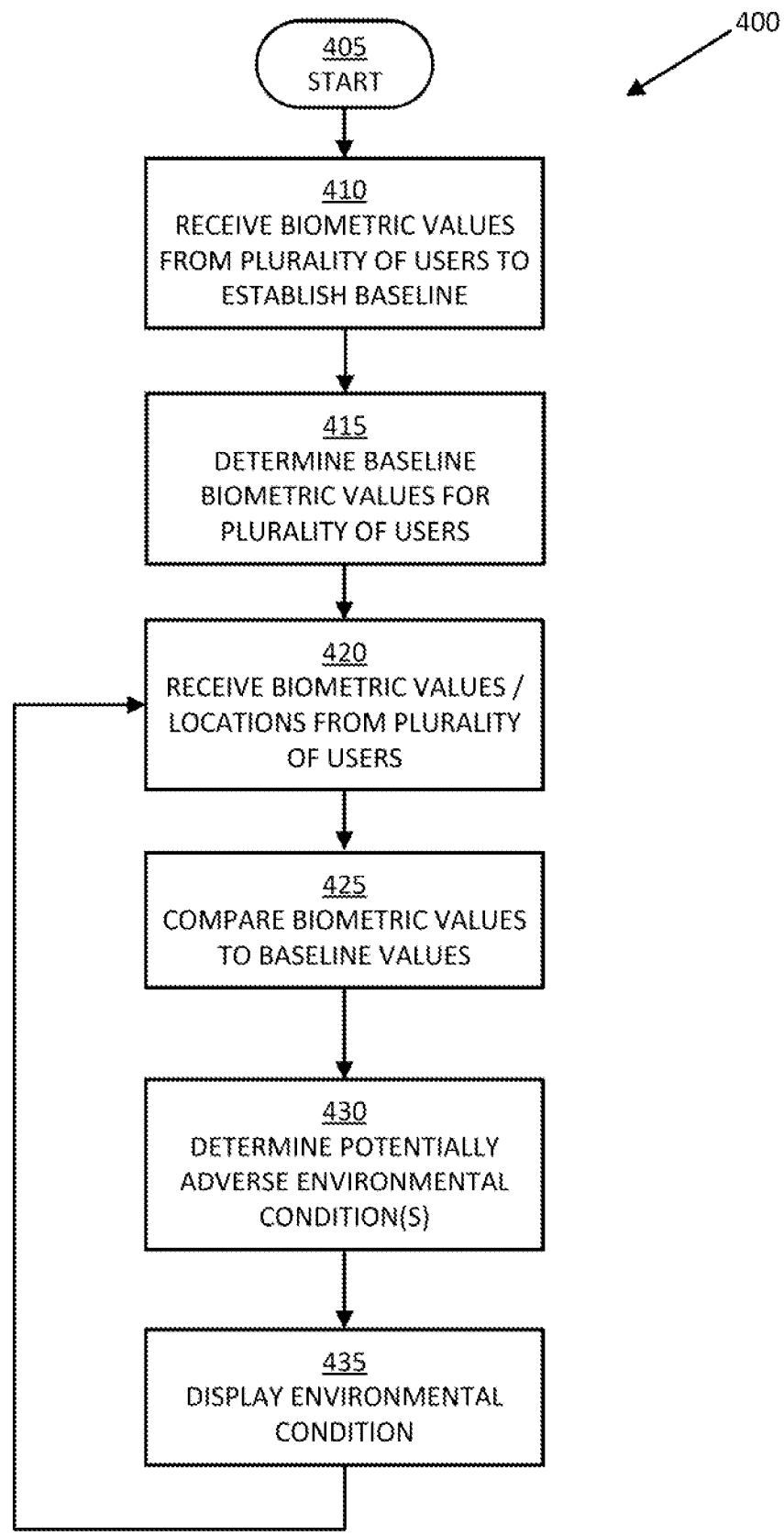
FIG. 4 is an example flowchart illustrating an example method for monitoring environmental conditions in accordance with example embodiments of the present disclosure.

Reference will now be made to FIG. 4, which provides a flowchart illustrating example steps, processes, procedures, and/or operations in accordance with various embodiments of the present disclosure. Various methods described herein, including, for example, example methods as shown in FIG. 4, may provide various technical benefits and improvements. It is noted that each block of the flowchart, and combinations of blocks in the flowchart, may be implemented by various means such as hardware, firmware, circuitry and/or other devices associated with execution of software including one or more computer program instructions. For example, one or more of the procedures described in FIG. 4 may be embodied by computer program instructions, which may be stored by a non-transitory memory of an apparatus employing an embodiment of the present disclosure and executed by a processor in the apparatus. These computer program instructions may direct a computer or other programmable apparatus to function in a particular manner, such that the instructions stored in the computer-readable storage memory produce an article of manufacture, the execution of which implements the function specified in the flowchart block(s).

As described above and as will be appreciated based on this disclosure, embodiments of the present disclosure may be configured as methods, mobile devices, backend network devices, and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Similarly, embodiments may take the form of a computer program code stored on at least one non-transitory computer-readable storage medium. Any suitable computer-readable storage medium may be utilized including non-transitory hard disks, CD-ROMs, flash memory, optical storage devices, or magnetic storage devices.

Referring now to FIG. 4, an example method is illustrated. In some embodiments, the example method detects potentially hazardous environmental conditions by analyzing biometric signals, and corresponding user locations, from two or more users who are wearing wearable devices capable of detecting such biometric signals and locations.

The example method 400 of FIG. 4 starts at step/operation 405. At step/operation 410, a processor (such as, but not limited to, the processing circuitry 305 of the central monitoring device 105 described above in connection with FIG. 3) receives biometric signals from a plurality of users to establish a baseline for the biometric signals. As described further below, these baseline biometric signal values may be compared to biometric signal values collected in a workplace during work activities for detecting potentially hazardous environmental conditions. In some embodiments, the biometric signals are captured and sent to the central monitoring device 105 by each of a plurality of wearable devices 110 worn by respective users.

In some embodiments, the biometric signals for determining a baseline are captured under controlled conditions. For example, the biometric signals for determining a baseline may be captured in a location in which it is known that there are no potentially hazardous environmental conditions. In some embodiments, the biometric signals for determining a baseline may be captured while the users perform different activities, such as sitting, standing, walking, etc. In some embodiments, multiple biometric signals are captured for each user for use in determining a baseline. In some embodiments, such multiple biometric signals for determining a baseline may be captured at predefined intervals (e.g., every one minute or every five minutes) and may be captured over one session or over multiple different sessions.

At step/operation 415, a processor (such as, but not limited to, the processing circuitry 305 of the central monitoring device 105 described above in connection with FIG. 3) uses the multiple biometric signals for each user captured at step/operation 410 to determine a baseline for each user. The baseline for each user may be determined in any suitable manner and may be a single value or a range of values. For example, in some embodiments the baseline may comprise an average (mean) value of the biometric signals from a user or a range of values (for example, within three standard deviations of the mean value, or within the minimum and maximum values) of the biometric signals from a user. For some biometric signals, such as SpO2, the concern would be decreases in the biometric signal value so the baseline for such a biometric signal might be set at minus three standard deviations from mean. For some biometric signals, such as body temperature, the concern would be increases in the biometric signal value so the baseline for such a biometric signal might be set at plus three standard deviations from mean. For some biometric signals, such as pulse or respiratory rate, the concern would be both increases and decreases in the biometric signal value so the baseline for such a biometric signal might be set at plus/minus three standard deviations from mean. In some embodiments, steps/operations 410 and 415 may be performed initially for all users and then performed as needed for any new users. In some embodiments, the wearable devices are able to detect if a user is stationary (sitting or standing) or is moving around (walking or running). In such embodiments, the central monitoring device can set different baselines for sitting/standing and walking/running.

At step/operation 420, a processor (such as, but not limited to, the processing circuitry 305 of the central monitoring device 105 described above in connection with FIG. 3) receives biometric signals and associated locations for each of a plurality of users according to a predetermined schedule/plan, in order to detect potentially hazardous environmental conditions such as in a workplace. In some embodiments, the biometric signals are captured and sent to the central monitoring device 105 by each of a plurality of wearable devices 110 worn by respective users. In some embodiments, each user may don and activate a wearable device 110 at the start of the user's workday and wear the device during the workday. In some embodiments, each of the wearable devices 110 will capture one or more biometric signals from the respective user continuously or at predetermined intervals (e.g., every minute or every five minutes) while the device is worn and activated. In some embodiments, the frequency of biometric signal capture is selected based at least in part on the expected battery life of the wearable device. In one example embodiment, the frequency of biometric signal capture may be selected such that the wearable device's battery (which is typically rechargeable) would last an entire workday. In some embodiments, every time the wearable device captures a biometric signal from the respective user, the wearable device also captures the user's location at the time the biometric signal was captured.

In some embodiments, every time the wearable device captures a biometric signal from the respective user and an associated location, the wearable device transmits that data to the central monitoring device. In some other embodiments, the wearable device may capture a biometric signal from the respective user and an associated location multiple times and store that data on the wearable device temporarily until the wearable device transmits that data to the central monitoring device at a later time. In one example embodiment, each of the wearable devices 110 may capture the biometric signals and locations every minute, but only transmit that data to the central monitoring device every five minutes to conserve battery life. In yet some other embodiments, the wearable device may capture a biometric signal from the respective user and an associated location multiple times and store that data on the wearable device temporarily until the wearable device detects an event (such as a decrease in the user's SpO2) which prompts the wearable device to transmit the stored data to the central monitoring device.

In some embodiments, the wearable devices 110 may capture each user's location at any suitable granularity, depending at least in part on the capability of the location sensing circuitry 225. In one example embodiment, the wearable devices 110 may capture each user's location within one square meter.

Figure 5:
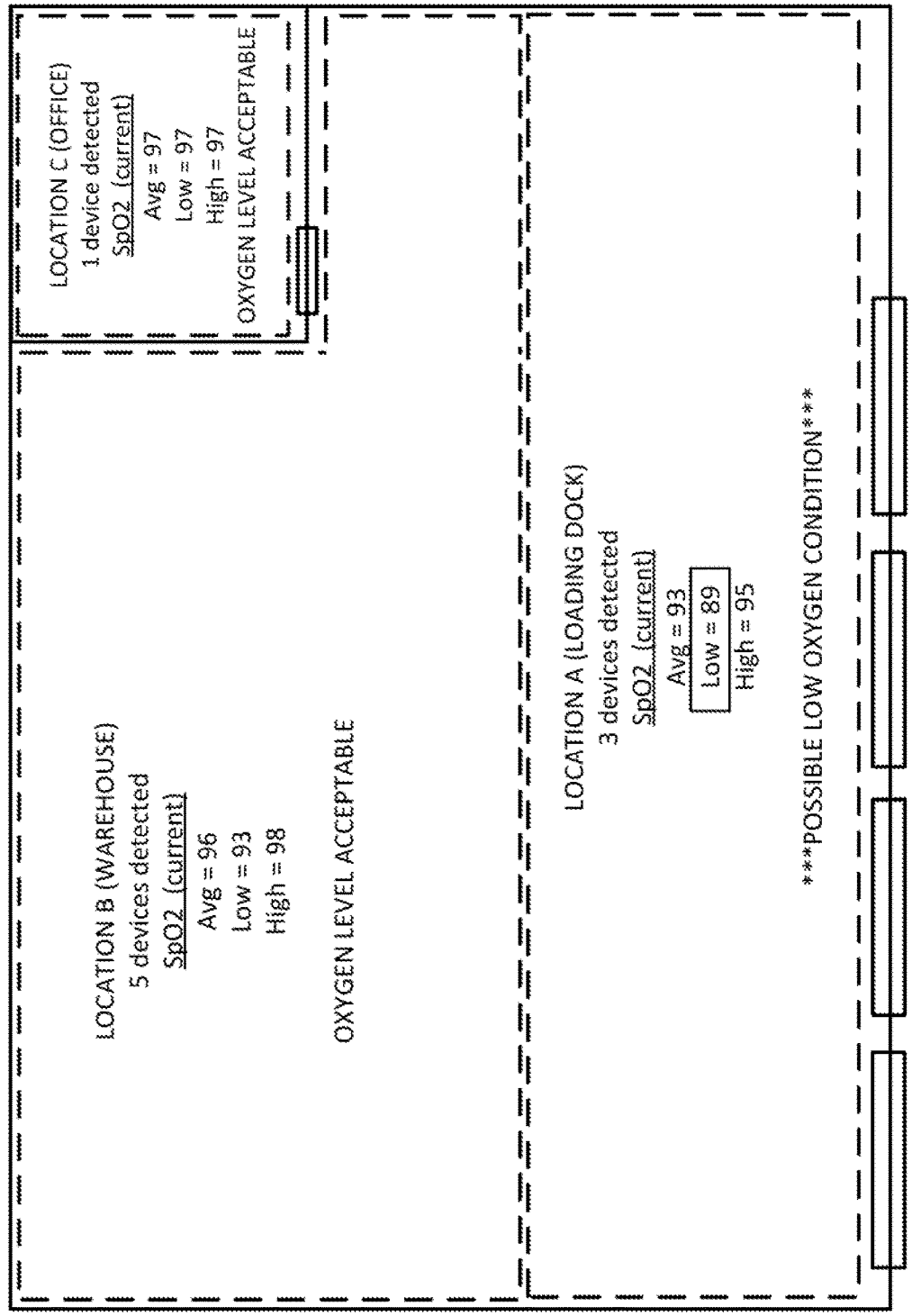
FIG. 5 illustrates an example user interface for monitoring environmental conditions, in accordance with at least some example embodiments of the present disclosure.

In some embodiments, a processor (such as, but not limited to, the processing circuitry 305 of the central monitoring device 105 described above in connection with FIG. 3) converts each of the received locations from the precise values received (e.g., the one square meter specific user locations) into a corresponding predefined area within the workplace. This conversion enables the workplace environment to be analyzed according to subdivided areas. Such subdivisions would typically be established during the initial set up of an environmental monitoring system of embodiments of the disclosure (such as, but not limited to, the system 100 described above in connection with FIG. 1). Such subdivisions may be established based, at least in part, on the structural/architectural elements (e.g., walls, doors, windows, vents, etc.) of different areas within the workplace that might affect the environmental conditions. Such an example embodiment is shown in FIG. 5, in which a workplace has been subdivided into three different areas (demarcated by dashed lines): Location A is a loading dock; Location B is a warehouse; and Location C is an office.

At step/operation 425, a processor (such as, but not limited to, the processing circuitry 305 of the central monitoring device 105 described above in connection with FIG. 3) compares the received biometric signals for each of a plurality of users to the baselines determined at step/operation 415. In some embodiments, the nature of the comparison may vary depending on the form of the baseline. For example, if the baseline is an average, the comparison at step/operation 425 may determine if the received biometric signal is below the baseline (for a biometric signal for which a decrease may be a concern) or above the baseline (for a biometric signal in which an increase may be a concern). As another example, if the baseline is a range, the comparison at step/operation 425 may determine if the received biometric signal is below the range (for a biometric signal for which a decrease may be a concern) or above the range (for a biometric signal in which an increase may be a concern). As yet another example, if the baseline is an average, the comparison at step/operation 425 may determine if the received biometric signal is more than a predefined number of standard deviations below the baseline (for a biometric signal for which a decrease may be a concern) or more than a predefined number of standard deviations above the baseline (for a biometric signal in which an increase may be a concern). As yet another example, if the baseline is an average, the comparison at step/operation 425 may determine if the received biometric signal is more than a predefined percentage below the baseline (for a biometric signal for which a decrease may be a concern) or more than a predefined percentage above the baseline (for a biometric signal in which an increase may be a concern).

In some embodiments, in addition to detecting deviations of the biometric signals from baseline values, the processor may compare the received biometric signals to prior values from the same user or from multiple users in the same area (for example, by averaging the values from the multiple users) to detect changes (e.g., a downward trend) that may not have yet reached a predetermined threshold variance from the baseline. For example, if the processor is looking for a decrease from the baseline of more than three standard deviations, detecting such a downward trend may identify a potentially hazardous environmental condition before the threshold is reached.

At step/operation 430, a processor (such as, but not limited to, the processing circuitry 305 of the central monitoring device 105 described above in connection with FIG. 3) determines if any potentially hazardous environmental conditions exist based on the comparisons performed at step/operation 425. In some embodiments, the determination if any potentially hazardous environmental conditions exist is based on the comparisons of biometric values to baselines for two or more users. In some alternative embodiments, the determination if any potentially hazardous environmental conditions exist is based on the comparisons of biometric values to baselines for any one or more users. Such a determination if any potentially hazardous environmental conditions exist based on the comparisons of biometric values to baselines for two or more users may be performed in any suitable manner. For example, in some embodiments, a potentially hazardous environmental condition is determined to exist in an area if two or more (or any other suitable number) users in that area are determined to have biometric values that deviate from their respective baselines in a predefined manner (such as described above in relation to step/operation 425). As another example, in some embodiments, a potentially hazardous environmental condition is determined to exist in an area if ten percent (or any other suitable percentage) or more of users in that area are determined to have biometric values that deviate from their respective baselines in a predefined manner (such as described above in relation to step/operation 425). As yet another example, the biometric signals and baselines for all users in a specific area are combined (e.g., averaged), and a potentially hazardous environmental condition is determined to exist in an area if the combined biometric values of the users in that area are determined to deviate from the combined baselines in a predefined manner (such as described above in relation to step/operation 425). In some embodiments, such determination methods can be combined. For example, in some embodiments, a potentially hazardous environmental condition is determined to exist in an area if two or more (or any other suitable number) users in that area or if ten percent (or any other suitable percentage) or more of users in that area are determined to have biometric values that deviate from their respective baselines in a predefined manner (such as described above in relation to step/operation 425). In some embodiments, the threshold number of users varying from baseline needed to determine that a potentially hazardous environmental exists may vary based on the magnitude of the detected variance(s) from baseline. That is, in some embodiments, the larger the detected variance(s) from baseline, the fewer number of users varying from baseline are needed to determine that a potentially hazardous environmental exists. In some embodiments, the threshold number of users varying from baseline needed to determine that a potentially hazardous environmental exists may vary based on the number of users in an area. That is, for an area having a small number of users, a smaller number or percentage of users varying from baseline are needed to determine that a potentially hazardous environmental exists. Similarly, for an area having a large number of users, a larger number or percentage of users varying from baseline are needed to determine that a potentially hazardous environmental exists.

The determined potentially hazardous environmental condition is based on the type of biometric values that deviate from the baseline. In one example embodiment, a decrease in the SpO2 values for two or more users indicates a potentially hazardous decrease in the environmental oxygen level in the location of those users. In another example embodiment, an increase in the body temperatures of two or more users indicates a potentially hazardous increase in the environmental temperature in the location of those users. In yet another example embodiment, an increase or a decrease in the heart rates for two or more users indicates a potentially hazardous decrease in the environmental oxygen level in the location of those users.

In some embodiments, two or more different biometric signals may be captured from each user via the wearable devices and used to determine a potentially hazardous environmental condition. In such example embodiments, a potentially a potentially hazardous environmental condition may be determined if each of a predetermined number of the different biometric signals (which may be from each of one or more users in some embodiments or from each of two or more users in other embodiments) deviate from their respective baselines (such as in any one of the ways described above). For example, a potentially hazardous environmental condition may be determined if two different biometric signals (e.g., SpO2 and pulse) both deviate from their respective baselines. The number of different biometric signals from each user that must deviate from their respective baselines to determine a potentially hazardous environmental condition may be less than or equal to the total number of different biometric signals received from each user. For example, in some embodiments two different biometric signals are received from each user and both must deviate from their respective baselines to determine a potentially hazardous environmental condition. In an alternative example embodiment, four different biometric signals are received from each user but only two of them must deviate from their respective baselines to determine a potentially hazardous environmental condition.

In some embodiments, only the biometric signals from users (which may be from one or more users in some embodiments or from two or more users in other embodiments) are used to determine a potentially hazardous environmental condition, and no environmental sensors are used. At step/operation 435, a processor (such as, but not limited to, the processing circuitry 305 of the central monitoring device 105 described above in connection with FIG. 3) displays the environmental conditions (such as, but not limited to, on the display 325 of the central monitoring device 105 described above in connection with FIG. 3) for a user or users to view. In some embodiments, the users' biometric values may be displayed (individually or aggregated) regardless of whether a potentially hazardous environmental condition is detected. In some embodiments, if a potentially hazardous environmental condition is detected, an alert (visual and/or audio) may be produced by the central monitoring device 105.

In some embodiments, steps/operations 420 through 435 are continuously repeated, such as during an entire workday. As described above in relation to step/operation 420, in some embodiments steps/operations 420 through 435 are repeated continuously or at predetermined intervals (e.g., every minute or every five minutes) while the device is worn and activated.

Figure 6:
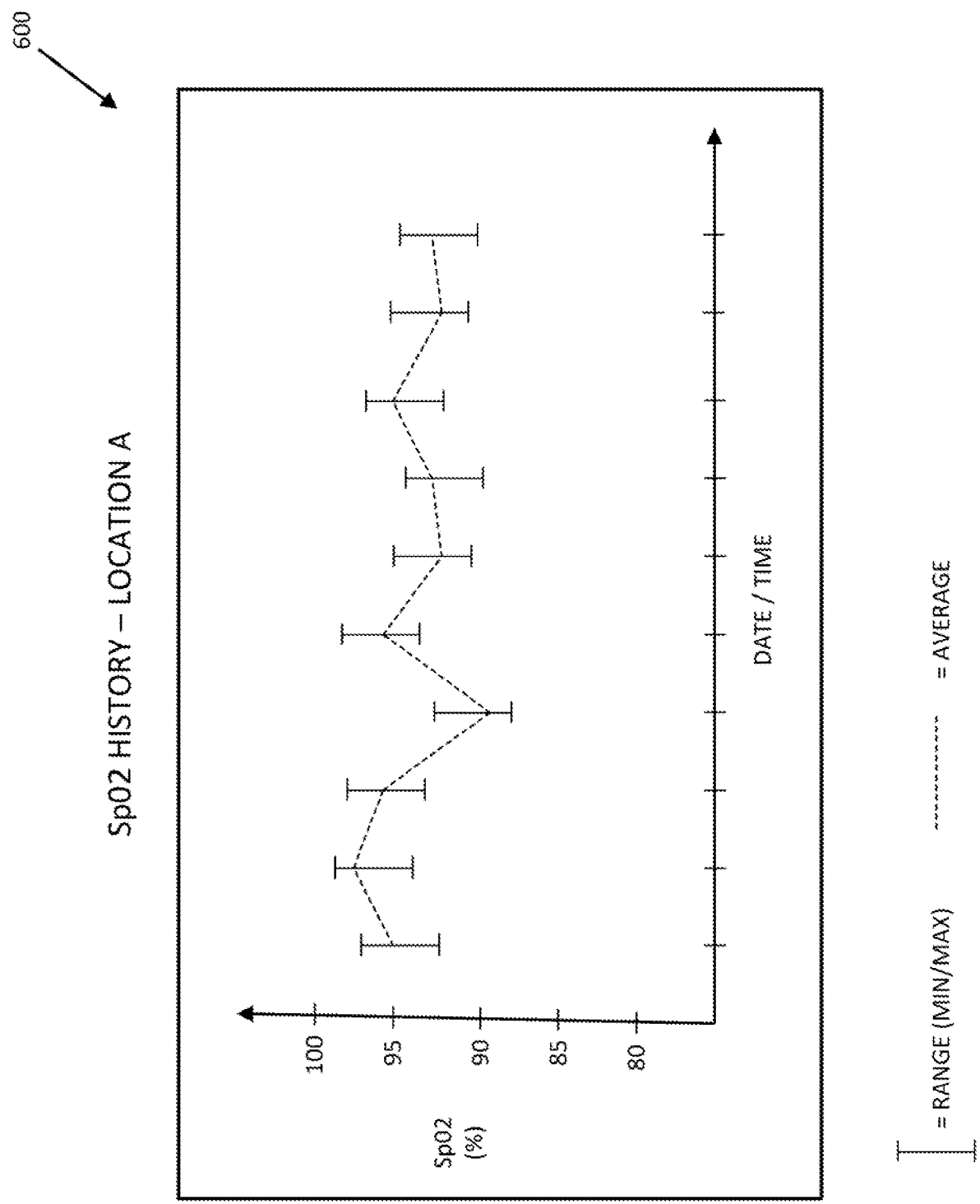
FIG. 6 illustrates another example user interface for monitoring environmental conditions.

FIGS. 5 and 6 illustrate example user interfaces associated with an example system for monitoring environmental conditions. The example user interfaces of FIGS. 5 and 6 may be rendered by one or more computing devices, for example the central monitoring device 105 may cause rendering of the example user interfaces to a display (such as display 325) or one or more client device(s) associated with the central monitoring device 105. For example, in some embodiments, the example user interfaces are rendered to a client device associated with a particular user to enable the user to view and/or otherwise interact with the example user interfaces.

The example user interface 500 of FIG. 5 is a graphical representation of example biometric values for nine users displayed on a map of the workplace. As described above, the example illustrated in FIG. 5 shows the workplace divided into three areas for monitoring. In the illustrated embodiment, the number of users, the biometric values of those users, and the determined environmental condition (e.g., acceptable oxygen level or potentially low oxygen level) are displayed for each demarcated area. In the illustrated embodiment, the example user interface 500 displays only the current biometric values.

In some embodiments, historical biometric values (by user and/or by area) may be viewed. The example user interface 600 of FIG. 6 is a graphical representation of example historical biometric values for Location A. In some embodiments, any previous determinations of potentially hazardous environmental conditions are also displayed.

It is to be understood that the disclosure is not to be limited to the specific embodiments disclosed, and that modifications and other embodiments are intended to be included within the scope of the appended claims. Although specific terms are employed herein, they are used in a generic and descriptive sense only and not for purposes of limitation, unless described otherwise.

The invention claimed is:

1. An apparatus comprising at least one processor and at least one non-transitory memory comprising program code, wherein the at least one non-transitory memory and the program code are configured to, with the at least one processor, cause the apparatus to at least:
   receive, over a first time period, a plurality of biometric values from each of a plurality of biometric monitoring devices, each of the plurality of biometric monitoring devices being worn by a different one of a plurality of users in a workplace, each of the plurality of biometric values being detected from one of the plurality of users and having an associated time of capture and an associated user location at time of capture;
   detect an environmental condition in at least a predefined area of the workplace based on the received biometric values corresponding to a plurality of users at a same user location in the predefined area;
   determine the environmental condition as a hazardous condition upon determining that a predetermined percentage of users of the plurality of users at the user location have at least one biometric value deviating from corresponding baseline biometric values; and
   in response to detecting the hazardous condition, generate an alert based on the detected environmental condition for one or more users associated with the user location.

2. The apparatus of claim 1, wherein the biometric monitoring devices comprise pulse oximeters and the biometric values comprise oxygen saturation values.

3. The apparatus of claim 1, wherein the at least one non-transitory memory and the program code are configured to, with the at least one processor, cause the apparatus to detect a change in the environmental condition based on one or more changes in the received biometric values corresponding to the at least two or more users at a same user location.

4. The apparatus of claim 1, wherein the at least one non-transitory memory and the program code are configured to, with the at least one processor, cause the apparatus to determine a baseline biometric value for each of the plurality of users by receiving, over a second time period and under one or more controlled conditions, a second plurality of biometric values from each of the plurality of biometric monitoring devices.

5. The apparatus of claim 4, wherein the apparatus is adapted to receive the second plurality of biometric values while a user of each of the plurality of biometric monitoring devices performs two or more different tasks.

6. The apparatus of claim 4, wherein the at least one non-transitory memory and the program code are configured to, with the at least one processor, cause the apparatus to detect the environmental condition based on the received biometric values corresponding to two or more users at the same user location by comparing the received biometric values corresponding to two or more users at the same user location to the corresponding baseline biometric value for the two or more users.

7. A computer-implemented method comprising:
   receiving, over a first time period, a plurality of biometric values from each of a plurality of biometric monitoring devices, each of the plurality of biometric monitoring devices being worn by a different one of a plurality of users in a workplace, each of the plurality of biometric values being detected from one of the plurality of users and having an associated time of capture and an associated user location at time of capture;
   detecting an environmental condition in at least a predefined area of the workplace based on the received biometric values corresponding to a plurality of users at a same user location in the predefined area;
   determining the environmental condition as a hazardous condition upon determining that a predetermined percentage of users of the plurality of users at the user location have at least one biometric value deviating from corresponding baseline biometric values; and
   in response to detecting the hazardous condition, generate an alert based on the detected environmental condition for one or more users associated with the user location.

8. The computer-implemented method of claim 7, wherein the biometric monitoring devices comprise pulse oximeters and the biometric values comprise oxygen saturation values.

9. The computer-implemented method of claim 7, further comprising detecting a change in the environmental condition based on one or more changes in the received biometric values corresponding to at least two or more users at a same user location.

10. The computer-implemented method of claim 7, further comprising determining a baseline biometric value for each of the plurality of users by receiving, over a second time period and under one or more controlled conditions, a second plurality of biometric values from each of the plurality of biometric monitoring devices.

11. The computer-implemented method of claim 10, wherein receiving, over a second time period and under one or more controlled conditions, a second plurality of biometric values from each of the plurality of biometric monitoring devices comprises receiving the second plurality of biometric values while a user of each of the plurality of biometric monitoring devices performs two or more different tasks.

12. The computer-implemented method of claim 10, wherein detecting an environmental condition based on the received biometric values corresponding to two or more users at a same user location comprises comparing the received biometric values corresponding to two or more users at the same user location to the corresponding baseline biometric value for the two or more users.

13. A computer program product comprising at least one non-transitory computer-readable storage medium having computer-readable program code portions stored therein, the computer-readable program code portions comprising an executable portion configured to:

receive, over a first time period, a plurality of biometric values from each of a plurality of biometric monitoring devices, each of the plurality of biometric monitoring devices being worn by a different one of a plurality of users in a workplace, each of the plurality of biometric values being detected from one of the plurality of users and having an associated time of capture and an associated user location at time of capture;

detect an environmental condition in at least a predefined area of the workplace based on the received biometric values corresponding to a plurality of users at a same user location in the predefined area;

determining the environmental condition as a hazardous condition upon determining that a predetermined percentage of users of the plurality of users at the user location have at least one biometric value deviating from corresponding baseline biometric values; and in response to detecting the hazardous condition, generate an alert based on the detected environmental condition for one or more users associated with the user location.

14. The computer program product of claim 13, wherein the biometric monitoring devices comprise pulse oximeters and the biometric values comprise oxygen saturation values.

15. The computer program product of claim 13, wherein the computer-readable program code portions comprise the executable portion configured to detect a change in the environmental condition based on one or more changes in the received biometric values corresponding to at least two or more users at a same user location.

16. The computer program product of claim 13, wherein the computer-readable program code portions comprise the executable portion configured to determine a baseline biometric value for each of the plurality of users by receiving, over a second time period and under one or more controlled conditions, a second plurality of biometric values from each of the plurality of biometric monitoring devices.

17. The computer program product of claim 16, wherein the computer-readable program code portions comprise the executable portion configured to receive the second plurality of biometric values while a user of each of the plurality of biometric monitoring devices performs two or more different tasks.

18. The computer program product of claim 16, wherein the computer-readable program code portions comprise the executable portion configured to detect the environmental condition based on the received biometric values corresponding to two or more users at the same user location by comparing the received biometric values corresponding to two or more users at the same user location to the corresponding baseline biometric value for the two or more users.

* * * * *